(12) United States Patent
Howat et al.

(10) Patent No.: US 9,855,095 B2
(45) Date of Patent: *Jan. 2, 2018

(54) MEDICAL DEVICE HAVING LAMINATE-COATED BRAID ASSEMBLY

(71) Applicant: St. Jude Medical, Atrial Fibrillation Division, Inc., St. Paul, MN (US)

(72) Inventors: Robert F. Howat, Excelsior, MN (US); Alan Fuentes, Mound, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/723,068

(22) Filed: May 27, 2015

(65) Prior Publication Data

US 2015/0374433 A1   Dec. 31, 2015

Related U.S. Application Data

(60) Continuation of application No. 14/486,456, filed on Sep. 15, 2014, now Pat. No. 9,060,785, which is a
(Continued)

(51) Int. Cl.
*A61B 18/14* (2006.01)
*A61M 25/00* (2006.01)
(Continued)

(52) U.S. Cl.
CPC .......... *A61B 18/1492* (2013.01); *A61B 5/042* (2013.01); *A61B 5/6852* (2013.01);
(Continued)

(58) Field of Classification Search
CPC ............ A61M 25/005; A61M 25/0045; A61M 25/0012; A61M 25/0053
See application file for complete search history.

(56) References Cited

U.S. PATENT DOCUMENTS 4,484,586 A   11/1984   McMickle et al.
4,840,186 A   6/1989    Lekholm et al.
(Continued)

FOREIGN PATENT DOCUMENTS

WO   2010/099096   9/2010

OTHER PUBLICATIONS

Definition of "transducer" by Merriam-Webster, Retrieved Jul. 25, 2016, "http://www.merriam-webster.com/dictionary/transducer".*
(Continued)

*Primary Examiner* — Nathan R Price
*Assistant Examiner* — Ahn Bui
(74) *Attorney, Agent, or Firm* — Wiley Rein LLP

(57) ABSTRACT

A catheter includes a braid assembly having a dual-laminate coating. The braid assembly includes a plurality of braid members interwoven to provide for interstices between the braid members, each braid member having an electrically conductive element, a flexible non-electrically-conductive polymer coating that insulates the electrically conductive element and a thermoplastic bonding adhesive coating. The braid assembly is formed between an inner polymer layer and an outer polymer layer. One or more of the braid members may be coupled to an energy delivery element.

19 Claims, 5 Drawing Sheets

Related U.S. Application Data division of application No. 12/392,821, filed on Feb. 25, 2009, now Pat. No. 8,864,744.

(51) Int. Cl.

| | | |
|---|---|---|
| *A61N 1/05* | (2006.01) | |
| *B32B 37/12* | (2006.01) | |
| *B32B 38/00* | (2006.01) | |
| *B32B 38/08* | (2006.01) | |
| *A61B 5/042* | (2006.01) | |
| *A61B 5/00* | (2006.01) | |
| *A61B 18/18* | (2006.01) | |
| *A61B 18/00* | (2006.01) | |
| *A61N 7/00* | (2006.01) | |

(52) U.S. Cl.

CPC ....... *A61B 18/1815* (2013.01); *A61M 25/005* (2013.01); *A61M 25/0012* (2013.01); *A61M 25/0045* (2013.01); *A61N 1/05* (2013.01); *B32B 37/1284* (2013.01); *B32B 38/00* (2013.01); *B32B 38/08* (2013.01); *A61B 18/18* (2013.01); *A61B 2018/00083* (2013.01); *A61B 2018/00107* (2013.01); *A61B 2018/00136* (2013.01); *A61B 2018/00577* (2013.01); *A61B 2018/1861* (2013.01); *A61N 7/00* (2013.01)

(56) References Cited

U.S. PATENT DOCUMENTS

| | | | |
|---|---|---|---|
| 5,456,259 A * | 10/1995 | Barlow | A61B 8/12 600/459 |
| 5,522,875 A | 6/1996 | Gates et al. | |
| 5,591,142 A * | 1/1997 | Van Erp | A61B 5/6852 604/264 |
| 5,658,264 A | 8/1997 | Samson | |
| 5,843,031 A | 12/1998 | Hermann et al. | |
| 5,843,076 A | 12/1998 | Webster, Jr. et al. | |
| 5,906,605 A | 5/1999 | Coxum | |
| 5,938,603 A | 8/1999 | Ponzi | |
| 6,165,163 A * | 12/2000 | Chien | A61M 25/0053 604/523 |
| 6,171,275 B1 | 1/2001 | Webster, Jr. | |
| 6,210,406 B1 | 4/2001 | Webster | |
| 6,213,995 B1 * | 4/2001 | Steen | A61B 18/14 604/527 |
| 6,217,573 B1 | 4/2001 | Webster | |
| 6,217,574 B1 | 4/2001 | Webster | |
| 6,277,077 B1 | 8/2001 | Brisken et al. | |
| 6,702,811 B2 | 3/2004 | Stewart et al. | |
| 7,354,428 B1 * | 4/2008 | Gosiengfiao | A61M 25/005 604/500 |
| 8,864,744 B2 * | 10/2014 | Howat | A61N 1/05 600/373 |
| 9,060,785 B2 * | 6/2015 | Howat | A61N 1/05 |
| 2002/0058978 A1 | 5/2002 | Sass | |
| 2004/0102804 A1 | 5/2004 | Chin | |
| 2005/0004643 A1 * | 1/2005 | Ebert | A61L 31/10 607/122 |
| 2008/0015517 A1 | 1/2008 | Geistert et al. | |
| 2008/0161762 A1 | 7/2008 | Stehr et al. | |

OTHER PUBLICATIONS

International Search Report and Written Opinion for PCT/US10/25017 dated Apr. 13, 2010.

Supplemental European Search Report for EP10746697 dated Oct. 19, 2012.

* cited by examiner

MEDICAL DEVICE HAVING LAMINATE-COATED BRAID ASSEMBLY

The present application is a continuation of U.S. application Ser. No. 14/486,456, filed 15 Sep. 2014, now pending, which is a division of U.S. patent application Ser. No. 12/392,821, filed 25 Feb. 2009, now U.S. Pat. No. 8,864,744. Each of the forgoing is hereby incorporated by reference as though fully set forth herein.

BACKGROUND OF THE INVENTION

Field of the Invention

The present invention pertains generally to electrophysiological devices and methods for diagnosing and treating biological tissue and, more particularly, to diagnostic and therapeutic catheters having a laminate-coated braid assembly.

Background Art

Catheters are used for an ever-growing number of procedures. For example, catheters are used for diagnostic, therapeutic, and ablative procedures, to name just a few examples. Typically, the catheter is manipulated through a patient's vasculature and to the intended site, for example, a site within the patient's heart. The catheter typically carries one or more electrodes, which may be used for ablation, diagnosis, or the like.

Since the path through the patient's vasculature to the intended site is often long and tortuous, steering forces typically must be transmitted over relatively great distances. Accordingly, it is desirable for a catheter to have sufficient flexibility to substantially conform to the patient's vasculature and yet resist kinking as it does so. Kinking is often the result of a localized failure of the material of the catheter when localized stresses exceed the yield strength of the material. To provide flexibility and kink resistance, many extant catheters include metallic wire braiding.

Many catheters also include one or more electrical wires for energizing electrodes or other energy delivery or diagnostic elements. The electrical wires must be insulated from the wire braiding, if present, and other internal components in order to prevent electrical shorts. In some cases, the braid wires may serve as the electrical wires. In order for braid wires to be implemented as the electrical wires, the braid wires must be insulated, otherwise contact between adjacent braid wires may induce electrical shorts. Most existing insulative coatings are too stiff for use in steerable devices and tend to result in tears that cause electrical shorts after only a few articulations of the device, for example as few as 10-12 articulations. What is needed, therefore, are flexible braid assemblies having insulated braid members that can withstand a greater number of articulations without tearing.

BRIEF SUMMARY OF THE INVENTION

The present invention provides for catheters having improved braid wire assemblies.

An object of the present invention is to provide catheters having braid wire assemblies that can be used to conduct electrical energy to one or more energy delivery elements.

Another object of the present invention is to provide braid wire assemblies having improved coatings that impart both insulating properties and flexibility.

A further object of the present invention is to provide medical devices incorporating braid wire assemblies having insulative coatings with improved durability.

In one embodiment, a catheter shaft of the present invention includes an inner layer of a first polymeric material, an outer layer of a second polymeric material, and a braid assembly formed between the inner layer and the outer layer. The braid assembly includes a plurality of braid members interwoven to provide for interstices between the braid members, and each of the plurality of braid members includes an electrically conductive element having a first coating and a second coating. The first coating is made of a flexible non-electrically-conductive polymer that insulates the electrically conductive element, and the second coating is made of a thermoplastic bonding adhesive that bonds to the outer layer. The first coating may be a polyurethane material and may have a durometer in the range of Shore A-50 to Shore A-70. In one form, the first coating is selected for its flexibility to withstand more than 50 articulations. In another form, the first coating is selected for its flexibility to withstand more than 150 articulations. The second coating may be a polyamide material and may have a durometer in the range of Shore D-40 to Shore D-50.

The electrically conductive element may include a copper alloy or plated copper and/or at least one of steel, stainless steel, beryllium, nickel, cobalt, zinc, aluminum, tantalum, platinum, iridium, gold, and silver. In one aspect, the electrically conductive element includes about 0.5% to about 5% beryllium. In another aspect, the electrically conductive element is a flat wire. In a further aspect, the flat wire has rounded edges.

The catheter shaft may further include at least one energy delivery element disposed along a distal end of the shaft. In one aspect, the energy delivery element is a radiofrequency electrode, an ultrasound transducer, or a microwave element. Each energy delivery element may be coupled to one braid member. For example, a first of the plurality of braid members may be electrically coupled to a first of the energy delivery elements, and a second of the plurality of braid members may be electrically coupled to a second of the energy delivery elements. The catheter shaft may include 2-16 energy delivery elements.

In another embodiment, a catheter of the present invention includes an elongate catheter body having an outer surface, a proximal end, a distal end, and an inner lumen extending between the proximal and distal ends. One or more energy delivery elements are disposed along the distal end of the elongate catheter body. The catheter also includes a braid assembly extending from at or near the proximal end to at or near the distal end. The braid assembly includes a plurality of braid members interwoven to provide for interstices between the braid members, and each of the plurality of braid members includes an electrically conductive element having a first coating and a second coating. The first coating is made of a flexible non-electrically-conductive polymer that insulates the electrically conductive element, and the second coating is made of a heat sensitive bonding adhesive. At least one of the plurality of braid members is electrically coupled to each of the one or more energy delivery elements. In one aspect, the braid assembly is formed between an inner polymer layer and an outer polymer layer.

The electrically conductive element may include a copper alloy or plated copper and/or at least one of steel, stainless steel, beryllium, nickel, cobalt, zinc, aluminum, tantalum, platinum, iridium, gold, and silver. In one aspect, the electrically conductive element includes about 0.5% to about 5% beryllium. In another aspect, the electrically conductive element is a flat wire. In a further aspect, the flat wire has rounded edges.

The first coating may include a polyurethane material, and the second coating may include a polyamide material. In one aspect, the first coating is selected for its flexibility to withstand more than 50 articulations. In another aspect, the first coating is selected for its flexibility to withstand more than 150 articulations. The one or more energy delivery elements may be one of a radiofrequency electrode, an ultrasound transducer, and a microwave element. The catheter may include from 2-16 energy delivery elements.

A method of manufacturing a catheter includes the steps of forming an inner layer of a first polymer, forming a braided assembly layer about the inner layer, and forming an outer layer of a second polymer about the braided assembly layer. The braided assembly layer includes a plurality of braid members interwoven to provide for interstices between the braid members, and the step of forming the braided assembly layer includes providing a plurality of electrically conductive elements, coating the electrically conductive elements with a first coating, the first coating comprising a flexible non-electrically-conductive polymer that insulates the electrically conductive element, coating the electrically conductive elements with a second coating, the second coating comprising a heat sensitive bonding adhesive, and braiding the electrically conductive elements to form a braided assembly layer.

In one aspect, the method further includes heating the inner layer, the braided assembly layer and the outer layer to bond the inner layer, the braided assembly layer and the outer layer together. In another aspect, the method further includes introducing a heat-shrink tube about the outer layer prior to the heating step. The step of forming the inner layer may include extruding the inner layer about a core rod, and the step of forming the braided assembly layer about the inner layer may include braiding the braid members about the inner layer. Also, the step of forming the outer layer about the braided assembly layer may include extruding the outer layer about the braided assembly layer. The method may further include the step of forming at least one energy delivery element about a distal end of the outer layer and electrically coupling at least one of the braid members to the at least one energy delivery element.

An advantage of the present invention is that the braid wire assemblies can serve as the conductive element for one or more energy delivery elements, thus reducing the thickness of the catheter and increasing the usable inner diameter of the catheter.

Another advantage is that catheters made according to the present invention are sufficiently flexible to withstand a greater number of articulations without causing tears that lead to electrical shorts.

The foregoing and other aspects, features, details, utilities, and advantages of the present invention will be apparent from reading the following description and claims, and from reviewing the accompanying drawings.

DETAILED DESCRIPTION OF THE INVENTION

The present invention provides a catheter shaft suitable for use in the human vasculature for known medical procedures, such as cardiac mapping and ablation. For purposes of this description, the invention will be described in connection with an elongate electrophysiology catheter. It is contemplated, however, that the described features and methods may be incorporated into any number of devices (e.g., steerable catheters, introducers, sheaths, and the like) as would be appreciated by one of ordinary skill in the art.

Figure 1:
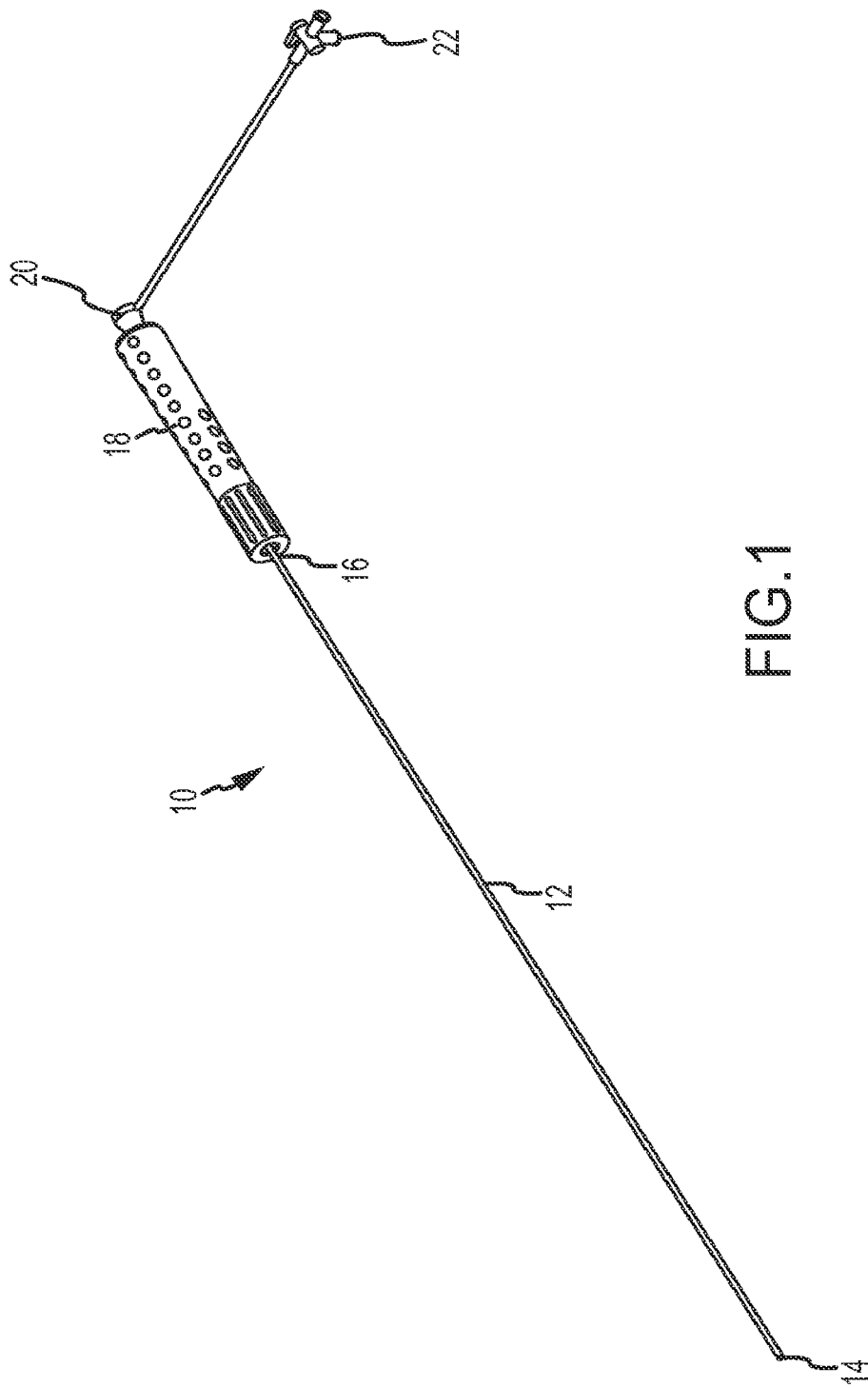
FIG. 1 is a perspective view of an exemplary catheter according to an embodiment of the present invention.

Referring now to FIG. 1, an electrophysiology catheter 10 includes a shaft 12 having a distal end 14 and a proximal end 16. A handle 18 may be coupled to the proximal end 16 of the shaft 12 to control the catheter 10 (e.g., to push and/or torque the catheter 10). The catheter 10 may also include a hub 20 operably coupled to an inner lumen (not shown) within the handle 18. A valve 22 may be operably connected to the hub 20. Of course, it is also contemplated that any known device for manipulation of the catheter 10 may be coupled to the proximal end 16, including, without limitation, robotic manipulation devices and the like.

Figure 8:
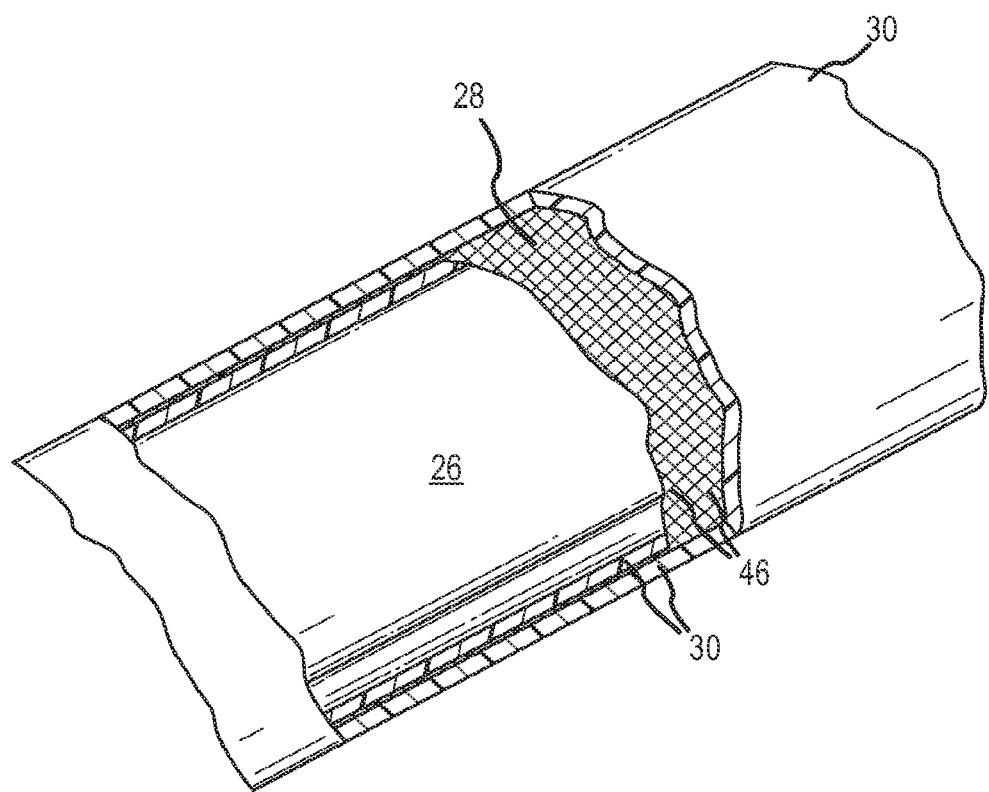
FIG. 8 illustrates a perspective view of a partially assembled catheter in accordance with an embodiment of the invention, cut away to show details.

As shown in FIG. 8, in one aspect, the catheter shaft includes an inner layer 26, a braid assembly 28, and an outer layer 30. The braid assembly 28 includes multiple braid members 46. Catheter shafts according to the present invention advantageously utilize improved braid assemblies having insulated braid members that are sufficiently flexible to withstand multiple catheter articulations without inducing tears in the insulative coating of the braid members. The braid assemblies of the present invention employ a dual-laminate coating over the braid members. A benefit of the described braid assemblies is that the braid members can serve as conductive elements for energizing electrodes or other energy-delivery elements present within the device. Even if not serving as conductive elements, the insulative coating on the braid members advantageously insulates the braid wires from other internal components within the catheter or device, thus reducing or eliminating the need for insulative layers elsewhere in the device, while at the same time maintaining a high degree of flexibility. The braid assemblies of the present invention also serve to reduce the overall thickness of the device and increase the usable space within the device.

Figure 2:
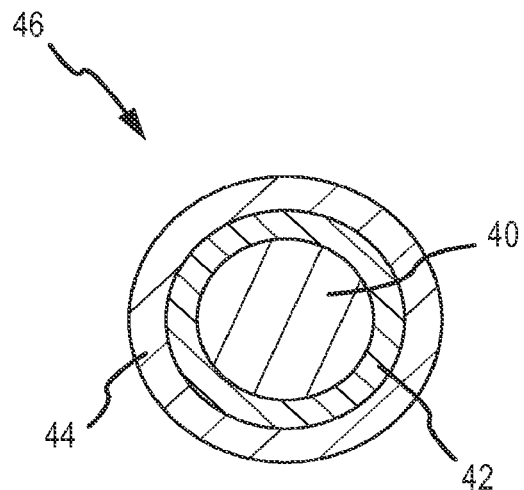
FIG. 2 is an axial cross-sectional view of a braid member according to an embodiment of the invention.
Figure 3:
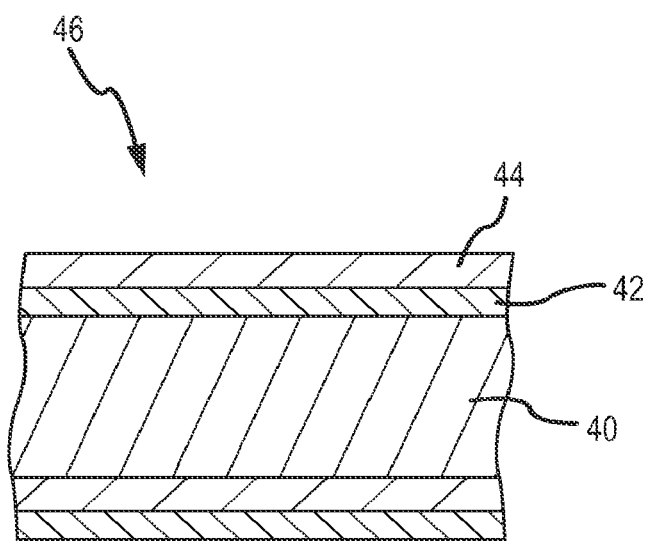
FIG. 3 is a longitudinal cross-sectional view of a braid member according to an embodiment of the invention.

As illustrated in FIGS. 2 and 3, the braid members 46 include a conductive element 40, a first coating 42 and a second coating 44. In one aspect, the conductive element 40 is an electrically conductive metallic material, such as a conductive wire, alloy or clad material. The conductive element 40 may include, for example, one or more of gold, silver, platinum, iridium, titanium, tantalum, zirconium, vanadium, niobium, hafnium, aluminum, silicone, tin, chromium, molybdenum, tungsten, lead, manganese, beryllium, iron, cobalt, nickel, palladium, osmium, rhenium, technetium, rhodium, ruthenium, cadmium, copper, zinc, germanium, arsenic, antimony, bismuth, boron, scandium and metals of the lanthanide and actinide series. In another aspect, the material used to manufacture the conductive element is a bio-compatible electrically conductive material, but other electrically conductive materials coated with bio-compatible materials may also be employed, including, for example, gold-plated copper. In another aspect, the conductive element 40 comprises a conductive fibrous material, for example, conductive Kevlar.

The conductive element 40 may be selected for its conductive properties as well as its strength and flexibility. In one aspect, the conductive element 40 is a copper alloy, or plated copper. For example, the conductive element 40 may be a copper alloy preferably having about 90% to about 99.5% copper and about 0.5% to about 10% beryllium, more preferably about 98% copper and about 2% beryllium. The conductive element 40 preferably has a tensile strength of about 150 to about 200 kpsi, more preferably about 170 kpsi.

In a further aspect, the conductive element 40 may be copper clad steel, for example, copper clad steel wherein the copper is about 99.5% pure copper and the steel is 1010 steel. In this aspect, the copper clad steel preferably has a volume of about 20% to about 60% copper and about 40% to about 80% steel, more preferably about 40% copper and about 60% steel and has an ultimate tensile strength of about 125 kpsi.

In another aspect, the conductive element 40 may be a flat wire or a round wire. For example, the conductive element 40 may be a flat wire having dimensions of about 0.0015" to about 0.005" by about 0.002" to about 0.020". For example, the conductive element 40 may have dimensions of about 0.001"×0.005", 0.002"×0.006", 0.003"×0.007", or 0.0015"×0.008". These dimensions are merely exemplary as a person of skill in the art will be able to select an appropriately sized conductive element for particular applications. After application of the dual laminate coating (i.e., the first coating 42 and the second coating 44), the overall dimensions of the conductive element 40 increase by about 0.00025" to about 0.00100" in each direction. In another aspect, the flat wire may have rounded edges. A flat wire with rounded edges is advantageous because the rounded or "soft" edges reduce the risk of tearing. In a further aspect, the conductive element 40 is a round wire having a diameter of about 0.0005" to about 0.005".

The first coating 42 is a flexible, non-electrically-conductive polymer that insulates the wire 40. The first coating 42 is selected for its flexibility. In other words, the first coating 42 is a flexible coating that moves with the braid assembly during catheter articulation and minimizes friction between the conductive element 40 and the first coating 42 during articulation. The first coating 42 is also selected for its dielectric properties to insulate the conductive element 40 from other braid members and from other internal components within the device. In one aspect, the first coating is a polyurethane material. The polyurethane material may have a durometer in the range of about Shore A 50-70, and a melt temperature of about 350° F. to about 400° F. In another aspect, the first coating 42 is a polyimide material having a melt temperature of about 450° F. to about 500° F.

The second coating 44 is a thermoplastic bonding adhesive. The second coating 44 increases the bonding of the braid assembly 28 to an outer polymer layer 30, described in more detail below, and thus decreases the friction between the braid assembly 28 and the outer layer 30. This results in a catheter assembly that can withstand a substantially larger number of articulations without causing tears in the first and second coatings. In one aspect, the second coating comprises a thermoplastic polyamide. The thermoplastic polyamide may have a durometer in the range of about Shore D 40-50. The second coating 44 has a melt temperature of about 300° F. to about 350° F. One example of a suitable material for the second coating 44 is Kanthal™ Bond M-A.

The first coating 42 and the second coating 44 may be applied to the conductive element 40 in a number of ways, for example using a roller or spray process. In one aspect, the coatings are applied using a two-dimensional (i.e., horizontal and vertical) coating process to achieve a more uniform application, especially at or near the edges of the conductive element. The dual laminate coating comprising the first coating 42 and the second coating 44 is advantageous in several respects. For example, the combination of the first coating 42 and the second coating 44 provide unique mechanical properties to aid with spring-back during catheter articulation. In addition, braid assemblies incorporating the dual laminate coating comprising the first coating 42 and the second coating 44 have fewer tears after multiple articulations. Previous insulating coatings resulted in tears after as few as 10-12 catheter articulations. Catheter assemblies utilizing braid assemblies of the present invention, however, can withstand at least 100 articulations, and preferably up to 200 articulations, without tearing.

The dual laminate coating of the present invention is also advantageous in that it allows the braid wire assembly to bond to an outer catheter layer to create a significant increased substrate structure between the braid assembly and the outer layer. The improved bonding of the braid assembly to the outer layer increases the effectiveness of catheter articulation.

A basic method of manufacturing the catheter 10, and in particular of at least a portion of the shaft 12, according to an embodiment of the present invention will be described with reference to FIGS. 4-7. As they are assembled, the catheter components will be collectively referred to as a "catheter shaft assembly."

Figure 4:
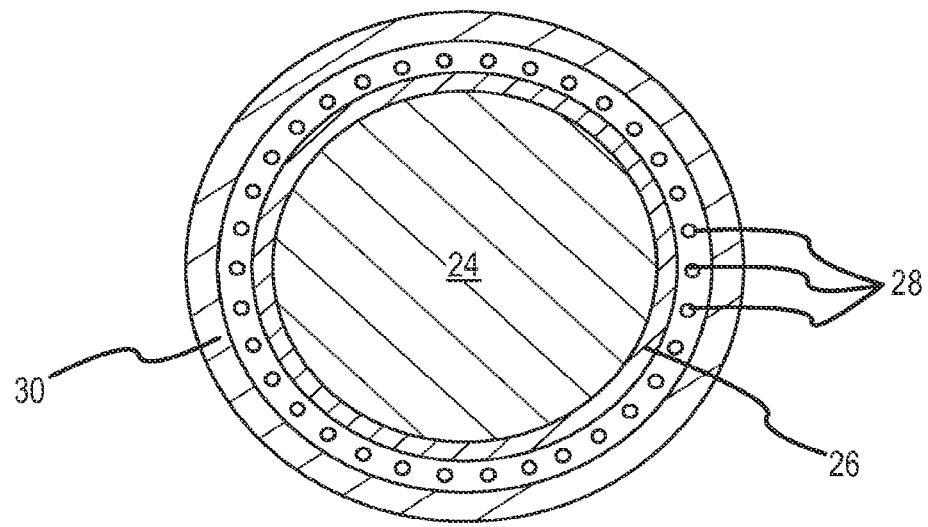
FIG. 4 depicts an axial cross-sectional view of the various components of a catheter shaft assembly according to an embodiment of the present invention prior to the application of heat to melt process the catheter shaft assembly.

As depicted in FIG. 4, a mandrel 24, such as a hardened stainless steel mandrel or a core rod, is provided. The mandrel or core rod 24 may be round in cross-section and from about 6 inches to about 4 feet in length. The mandrel or core rod 24 has a distal end and a proximal end. An inner layer 26 is formed about the mandrel or core rod 24. In one embodiment, the inner layer 26 may be formed by extruding a polymer material about the mandrel or core rod 24. In another embodiment, the inner layer 26 may be separately extruded and then slipped about the mandrel or core rod 24.

The inner layer 26 may be an extruded polymeric tubing, such as pre-extruded (and optionally chemically-etched) polytetrafluoroethylene (PTFE) tubing (e.g., Teflon® brand tubing). Inner layer 26 may also be made of other melt-processable polymers, including, without limitation, fluorinated ethylene-propylene copolymer (FEP), perfluoroalkoxyethylene (PFA), poly(vinylidene fluoride), poly(ethylene-co-tetrafluoroethylene), nylon (for example Nylon 911) and other fluoropolymers with surface treatment such as chemical etching, plasma and corona treatment, and the like. For example, the inner layer 26 may be made of Pebax®, a polyether block amide made by Arkema, Inc. Pebax® of various durometers may be used, including, without limitation, Pebax 55D to Pebax 72D. Liquid crystal polymers (LCPs) are also suitable materials for the inner layer 26.

A braid assembly 28 may then be formed about inner layer 26. The braid assembly 28 includes multiple braid members 46 (see FIGS. 2-3) formed in a braid pattern. As discussed above with reference to FIGS. 2-3, the braid members 46 include a conductive element 40, a first coating 42 and a second coating 44. The braid assembly 28 may be formed in a standard braid pattern and density, for example, about 16 wires at about 45 to about 60 picks per inch ("PPI") density. Alternatively, a braid assembly may be used that is characterized by a varying braid density. For example, the braid assembly 28 may be characterized by a first braid density at proximal end 16 of the catheter shaft 12 and then transition to one or more different braid densities as the braid assembly 28 approaches distal end 14 of the catheter shaft 12.

The braid assembly 28 may be formed separately on a disposable core and slipped about the inner layer 26. Alternatively, the braid assembly 28 may be braided directly upon the inner layer 26. In addition, one or more portions of the braid assembly 28 may be heat tempered and cooled before incorporation into the catheter shaft assembly through methods that are known to those of ordinary skill in the art. The action of heat tempering may help to release the stress on the conductive element 40 and help reduce radial forces.

An outer layer 30 may be formed about the braid assembly 28. The outer layer 30 may be formed by extruding a polymer material about the braid assembly 28. In some embodiments of the invention, the outer layer 30 may be separately extruded and then slipped about the braid assembly 28, such as illustrated in FIG. 4.

The outer layer 30 is typically a melt-processable polymeric tube, such as an extruded polytetrafluoroethylene (PTFE) tubing (e.g., Teflon® brand tubing), optionally with surface chemical etching. One of ordinary skill will appreciate that the outer layer 30 may also be made of other melt-processable fluoropolymers, including, without limitation, fluorinated ethylene-propylene copolymer (FEP), perfluoroalkoxyethylene (PFA), poly(vinylidene fluoride), poly(ethylene-co-tetrafluoroethylene), and the like with surface treatment. The outer layer 30 may also be made of melt processable thermoplastic elastomers with sufficiently high mechanical strength and rigidity, including, without limitation, nylon (for example, Nylon 911), polyamide-based thermoplastic elastomers (namely poly(ether-block-amide), polyester-based thermoplastic elastomers (e.g., Hytrel®), thermoplastic polyurethanes (e.g., Pellethane®, Estane®), and the like, and any combinations thereof. For example, the outer layer 30 may be made of Pebax®, a polyether block amide made by Arkema, Inc. Pebax® of various durometers may be used, including, without limitation, Pebax 55D to Pebax 72D. Liquid crystal polymers (LCPs) are also suitable materials for the outer layer 30.

Figure 5:
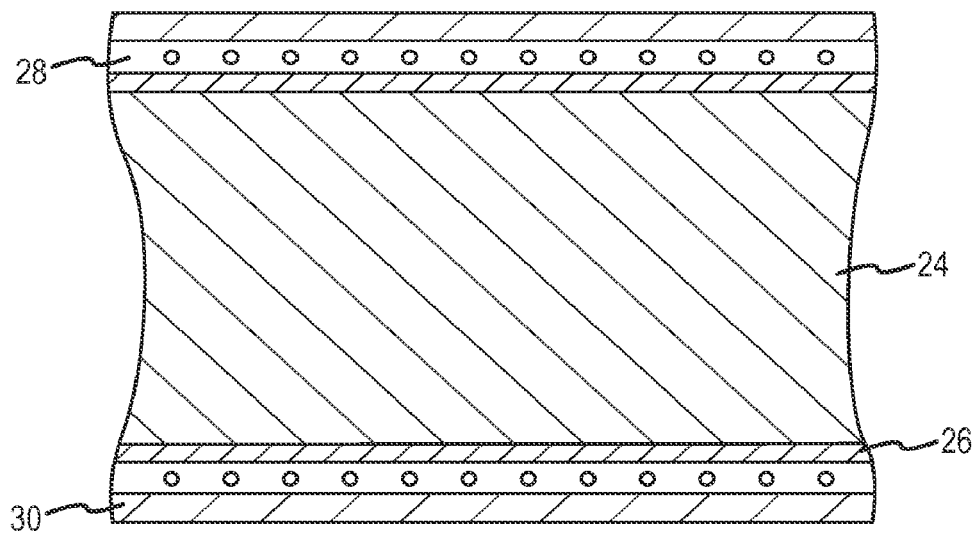
FIG. 5 is a longitudinal cross-sectional view of the various components of a catheter shaft assembly according to an embodiment of the present invention prior to the application of heat to melt process the catheter shaft assembly.
Figure 6:
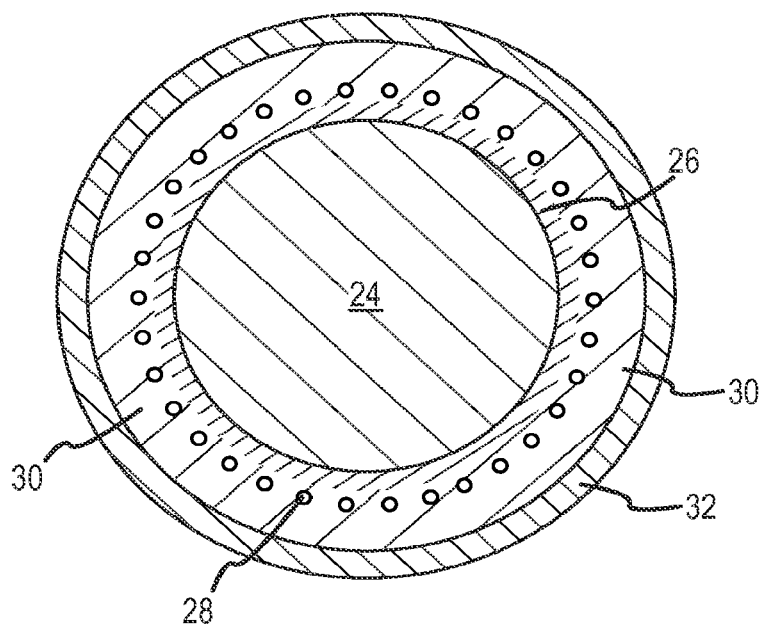
FIG. 6 is an axial cross-sectional view of a catheter shaft assembly according to an embodiment of the invention during the application of heat to melt process the catheter shaft assembly.

FIG. 4 displays an axial-cross section of the catheter shaft assembly including mandrel 24, inner layer 26, braid assembly 28, and outer layer 30 before thermal lamination of the various layers by heating (e.g., reflow bonding). FIG. 5 depicts a longitudinal cross-section of the catheter shaft assembly at the same stage of manufacture. As shown in FIG. 6, the catheter shaft assembly may then be melt-processed. In some embodiments of the invention, a heat shrink tube 32 is placed over outer layer 30. The heat shrink tube 32 is preferably a fluoropolymer such as fluorinated ethylene-propylene copolymer (FEP). As an alternative to using a heat shrink tube 32, the catheter shaft assembly may be placed into a suitable mold prior to subsequent processing. Either the heat shrink tube 32 or a suitable mold may be generally referred to as a "shape retention structure," so named because it retains the overall shape of the catheter shaft assembly (that is, the generally circular axial cross-section) during melt-processing.

Energy (e.g., radiofrequency energy or thermal energy) is applied to the catheter shaft assembly, for example to the outer surface of the catheter shaft assembly, to bond inner layer 26, braid assembly 28 and outer layer 30 together in a process often referred to as "reflow bonding." The second coating 44 on the braid members 46 will bond to the outer layer 30. The heat shrink tube 32 has a higher melting or softening temperature than inner layer 26, second coating 44, and outer layer 30, such that, during the melting process, the heat shrink tube 32 will maintain its tubular shape and/or contract during the reflow process. The combination of applied energy and pressure exerted by the heat shrink tube 32 forces inner layer 26, second coating 44 on the braid assembly 28, and outer layer 30 to flow locally and redistribute about the circumference of the catheter shaft assembly and melt together.

Figure 7:
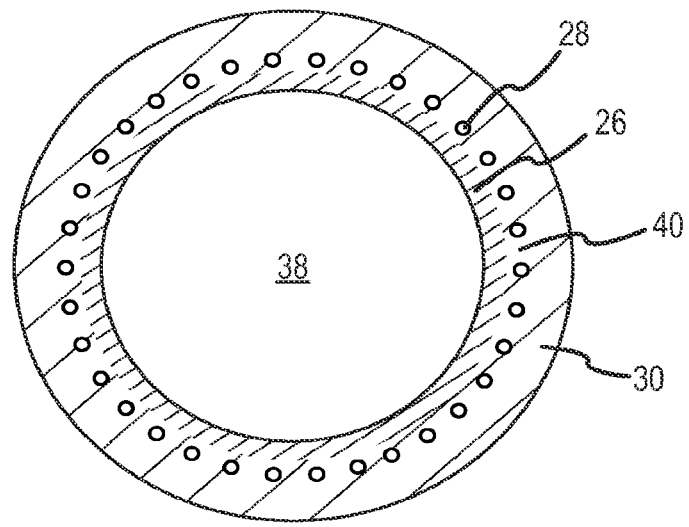
FIG. 7 is an axial cross-sectional view of a catheter shaft according to an embodiment of the invention after the application of heat to melt process the catheter shaft assembly.

Once the catheter shaft assembly has cooled, mandrel 24 can be removed, leaving a central lumen 38 (FIG. 7) extending through at least a portion of catheter shaft 12. Optionally, heat shrink tube 32 may also be removed, such that outer layer 30 becomes the outermost layer of the catheter shaft assembly. FIG. 7 depicts the catheter shaft assembly after the conclusion of the reflow bonding process (that is, FIG. 7 depicts an axial-cross section of a catheter shaft formed according to an embodiment of the present invention).

In one aspect, devices of the present invention include one or more energy delivery elements (not shown). Each energy delivery element may be coupled to at least one braid member, for example, using an epoxy. The energy delivery element may be a radiofrequency electrode, an ultrasound transducer or a microwave element. The devices of the invention may include a single energy delivery element, up to four energy delivery elements, up to eight energy elements, up to sixteen energy delivery elements, or more than sixteen energy delivery elements. As a person of skill in the art will appreciate, the braid pattern can be selected to accommodate various numbers of energy delivery elements.

Although multiple embodiments of this invention have been described above with a certain degree of particularity, those skilled in the art could make numerous alterations to the disclosed embodiments without departing from the spirit or scope of this invention. For example, the catheter assembly may include additional polymer layers in addition to the inner layer and outer layer. Further, helical windings may be used in place of the braid assembly.

All directional references (e.g., upper, lower, upward, downward, left, right, leftward, rightward, top, bottom, above, below, vertical, horizontal, clockwise, and counter-clockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A catheter comprising:
   an elongate catheter body having an outer surface, a proximal portion, a distal portion, and an inner lumen extending between the proximal and distal portions;
   an energy element disposed along the distal portion of the elongate catheter body; and
   a braid assembly extending from the proximal portion to the distal portion, the braid assembly comprising a plurality of braid members interwoven to provide for interstices between the braid members, wherein the density of the braid at the proximal portion is different from the density of the braid at the distal portion, and wherein at least one of the plurality of braid members comprises an electrically conductive element comprising a first coating comprising a flexible non-electrically-conductive polymer and a second coating comprising a thermoplastic bonding adhesive,
   wherein the electrically conductive element is electrically coupled to the energy element.

2. The catheter according to claim 1, wherein the braid assembly is formed between an inner polymer layer and an outer polymer layer.

3. The catheter according to claim 1, wherein the electrically conductive element comprises a copper alloy or plated copper.

4. The catheter according to claim 1, wherein the electrically conductive element is a flat wire.

5. The catheter according to claim 1, wherein a plurality of energy elements are disposed along the distal portion of the elongate catheter body.

6. A catheter comprising:
   an elongate catheter body having an outer surface, a proximal portion, a distal portion, and an inner lumen extending between the proximal and distal portions;
   a transducer disposed along the distal portion of the elongate catheter body; and
   a braid assembly extending from the proximal portion to the distal portion, the braid assembly comprising a plurality of braid members interwoven to provide for interstices between the braid members, wherein at least one of the plurality of braid members comprises an electrically conductive element comprising a first coating comprising a flexible non-electrically-conductive polymer and a second coating comprising a thermoplastic bonding adhesive,
   wherein at least one of the plurality of braid members is electrically coupled to the transducer.

7. The catheter according to claim 6, wherein a plurality of transducers are disposed along the distal portion of the elongate catheter body.

8. The catheter according to claim 6, wherein the braid assembly is formed between an inner polymer layer and an outer polymer layer.

9. The catheter according to claim 6, wherein the electrically conductive element comprises a copper alloy or plated copper.

10. The catheter according to claim 6, wherein the electrically conductive element is a flat wire.

11. A catheter comprising:
    an elongate catheter body having an outer surface, a proximal portion, a distal portion, and an inner lumen extending between the proximal and distal portions;
    a transducer disposed along the distal portion of the elongate catheter body; and
    a plurality of electrically conductive elements extending from the proximal portion to the distal portion, wherein each of the electrically conductive elements comprises a first coating comprising a flexible non-electrically-conductive polymer and a second coating comprising a thermoplastic bonding adhesive, and wherein the plurality of electrically conductive elements are in the shape of a helical winding, and
    wherein the transducer is electrically coupled to at least one of the plurality of electrically conductive elements.

12. The catheter according to claim 11, wherein the electrically conductive elements comprise a copper alloy or plated copper.

13. The catheter according to claim 11, wherein a plurality of transducers are disposed along the distal portion of the elongate catheter body.

14. The catheter according to claim 11, wherein the catheter further comprises a heat shrink layer surrounding the outer surface of the catheter body.

15. The catheter according to claim 11, wherein the transducer comprises an ultrasound transducer.

16. The catheter according to claim 11, wherein the transducer is electrically coupled to a plurality of electrically conductive elements.

17. The catheter according to claim 6, wherein the density of the braid at the proximal portion is different from the density of the braid at the distal portion.

18. The catheter according to claim 6, wherein the transducer is electrically coupled to a plurality of electrically conductive elements.

19. The catheter according to claim 6, wherein the transducer comprises an ultrasound transducer.

* * * * *